United States Patent
Beddard

(10) Patent No.: US 11,752,357 B2
(45) Date of Patent: Sep. 12, 2023

(54) PULSED ELECTROMAGNETIC FIELD THERAPY DEVICE

(71) Applicant: Hofmeir Magnetics Limited, Witney (GB)

(72) Inventor: Paul Beddard, Witney (GB)

(73) Assignee: Hofmeir Magnetics Limited, Witney (GB)

( * ) Notice: Subject to any disclaimer, the term of this patent is extended or adjusted under 35 U.S.C. 154(b) by 139 days.

(21) Appl. No.: 16/764,783

(22) PCT Filed: Nov. 16, 2018

(86) PCT No.: PCT/GB2018/053335
§ 371 (c)(1),
(2) Date: May 15, 2020

(87) PCT Pub. No.: WO2019/097254
PCT Pub. Date: May 23, 2019

(65) Prior Publication Data
US 2021/0370086 A1    Dec. 2, 2021

(30) Foreign Application Priority Data
Nov. 17, 2017 (GB) .................................... 1719104

(51) Int. Cl.
*A61N 2/02* (2006.01)
*A61N 2/00* (2006.01)

(52) U.S. Cl.
CPC ............. *A61N 2/02* (2013.01); *A61N 2/006* (2013.01)

(58) Field of Classification Search
CPC . A61N 2/02; A61N 2/006; A61N 1/40; A61N 2/00; A61N 2/002; A61N 2/004; A61N 2/008
See application file for complete search history.

(56) References Cited

U.S. PATENT DOCUMENTS 4,665,898 A * 5/1987 Costa ...................... A61N 2/02
600/14
4,940,453 A    7/1990 Cadwell
(Continued)

FOREIGN PATENT DOCUMENTS

CN    202478411 U    10/2012
CN    205598428 U    9/2016
(Continued)

OTHER PUBLICATIONS

LC Oscillator Basics, 10 pages printed from The Wayback Machine, Aug. 12, 2022, archived Jul. 9, 2015. (Year: 2015).*
(Continued)

*Primary Examiner* — Samuel G Gilbert
(74) *Attorney, Agent, or Firm* — HAYES AND BOONE, LLP

(57) ABSTRACT

A pulsed electromagnetic field therapy device has a parallel resonant circuit comprising a capacitor connected in parallel with an inductor without a switch between the capacitor and the inductor in the parallel resonant circuit. The parallel resonant circuit is configured to generate a pulsed electromagnetic field in the inductor while electrical energy is stored in the parallel resonant circuit, and the inductor is configured to be placed relative to a part of a body to provide the pulsed electromagnetic field to the part of the body. The device also has a power source. A switch, external to the parallel resonant circuit, selectively connects the parallel resonant circuit to the power source for a current ramping period, and during the current ramping period a current in the inductor is increased to reach a desired current.

17 Claims, 6 Drawing Sheets

(56) References Cited

U.S. PATENT DOCUMENTS

| | | | |
|---|---|---|---|
| 5,047,005 A | 9/1991 | Cadwell | |
| 5,314,400 A * | 5/1994 | Tsyb | A61N 2/02 600/14 |
| 6,083,149 A * | 7/2000 | Wascher | A61N 2/02 600/9 |
| 6,117,066 A | 9/2000 | Abrams et al. | |
| 6,123,658 A | 9/2000 | Schweighofer et al. | |
| 6,179,769 B1 * | 1/2001 | Ishikawa | A61N 2/006 128/DIG. 25 |
| 6,236,205 B1 | 5/2001 | Lüdeke et al. | |
| 7,162,293 B2 | 1/2007 | Weiss | |
| 7,744,523 B2 | 6/2010 | Epstein | |
| 10,463,870 B2 * | 11/2019 | Roth | A61N 2/02 |
| 2003/0026113 A1 | 2/2003 | Reilly et al. | |
| 2003/0158585 A1 * | 8/2003 | Burnett | A61N 2/008 607/2 |
| 2005/0134193 A1 | 6/2005 | Myers et al. | |
| 2006/0187607 A1 * | 8/2006 | Mo | A61N 2/02 361/143 |
| 2008/0125618 A1 * | 5/2008 | Anderson | A61N 2/02 600/14 |
| 2015/0333801 A1 | 11/2015 | Hosotani | |
| 2016/0184601 A1 * | 6/2016 | Gleich | A61N 2/006 600/14 |

FOREIGN PATENT DOCUMENTS

| | | | |
|---|---|---|---|
| DE | 2925878 A1 | 2/1991 | |
| EP | 0305791 A2 | 3/1989 | |
| EP | 2874297 A1 | 5/2015 | |
| EP | 3101779 A1 | 12/2016 | |
| GB | 1495391 A | 12/1977 | |
| GB | 2298370 A * | 9/1996 | A61N 2/02 |
| GB | 2395907 A | 6/2004 | |
| WO | WO-2014074638 * | 5/2014 | A61N 1/36025 |
| WO | WO-2016106736 A1 * | 7/2016 | A61B 18/12 |
| WO | WO-2018071906 A1 * | 4/2018 | A61N 2/006 |

OTHER PUBLICATIONS

Simple Parallel (Tank Circuit) Resonance, 8 pages printed from the Wayback machine Aug. 12, 2022, archived Nov. 4, 2015 (Year: 2015).*

Electronics Hub; LC Oscillator Basics, from internet The Wayback Machine, "www.electronicshub.org . . .", 14 pages, available on Oct. 26, 2015. (Year: 2015).*

Combined Search and Examination Report issued for GB1719104.0, dated Apr. 26, 2018, 9 pages.

International Search Report and Written Opinion issued for PCT/GB2018/053335 dated Feb. 21, 2019, 12 pages, ISA/EP.

* cited by examiner

PULSED ELECTROMAGNETIC FIELD THERAPY DEVICE

PRIORITY

The present application is a U.S. National Stage patent application of International Patent Application No. PCT/GB2018/053335, filed on Nov. 16, 2018, which claims priority to United Kingdom Application No. 1719104.0, filed on Nov. 17, 2017, the benefit of which is claimed and the disclosures of which are incorporated herein by reference in their entirety.

FIELD OF THE INVENTION

The present invention relates to a pulsed electromagnetic field therapy device. The present invention also relates to a method of generating a pulsed electromagnetic field which could be used to provide a physiological effect.

BACKGROUND OF THE INVENTION

Pulsed electromagnetic fields may be used to provide a physiological effects. For example, pulsed electromagnetic fields may be used for nerve or brain stimulation, or for providing therapeutic benefits (such as treating ailments like joint and muscle pain, and assisting with the healing of broken bones and fractures).

A number of pulsed electromagnetic field therapy devices are available which produce pulsed electromagnetic fields to provide a physiological effect. They typically include a resonant circuit formed from a capacitor connected to a coil looped inductor through a switch (such as a semiconductor or spark gap switch). With the switch open, the capacitor can be pre-charged before closing the switch to discharge the capacitor into the inductor to initiate oscillation of the resonant circuit. The resonant circuit then oscillates until losses dissipate the energy stored in the resonant circuit. As the resonant circuit oscillates, it generates a sequence of electromagnetic oscillations in the coil looped inductor which is placed adjacent to, or around, a part of the body where the physiological effect of the pulsed electromagnetic field is desired.

Existing pulsed electromagnetic field therapy devices operate at extremely high voltages (typically thousands of Volts). As a result of these high voltages, expensive high voltage capacitors and switches are required, which makes existing pulsed electromagnetic field therapy devices very expensive to manufacture. Additionally, the high voltages represent a safety risk to the operator and patient, particularly as the design of many existing pulsed electromagnetic field therapy devices are susceptible to lethal single point failures, for example, in a case where the insulation of the coil looped inductor becomes damaged. Therefore, it would be desirable to find a way to generate a pulsed electromagnetic field to provide a physiological effect in a way which eliminates the risks associated with these extremely high voltages.

Oscillations are damped by resistance losses in the components of the resonant circuit, particularly the semiconductor switch. As a result, existing pulsed electromagnetic field therapy devices are limited to a fairly short decay time, and it would be desirable to increase the decay time so that a physiological effect can be provided over a longer period.

It is common for existing pulsed electromagnetic field therapy devices to have a very high initial discharge current (typically many kAs). Voltage reflections from components in the resonant circuit, for example from a semiconductor switch which is nearly impossible to impedance match with the resonant circuit, result in high power and broad spectrum radio-frequency transmissions for the first few microseconds of the electromagnetic oscillations. Such radio-frequency interference causes existing pulsed electromagnetic field therapy devices to interfere with other electronic devices or wireless communications networks in the vicinity, and may mean that existing pulsed electromagnetic field therapy devices do not meet regulatory requirements, such as regulations regarding electromagnetic interference.

It would, therefore, be desirable to develop a pulsed electromagnetic field therapy device which overcomes, or at least mitigates, some or all of these problems.

SUMMARY OF THE INVENTION

According to a first aspect of the invention, there is provided a pulsed electromagnetic field therapy device. The parallel resonant circuit comprises a capacitor connected in parallel with an inductor without a switch between the capacitor and the inductor. That is, there is no switch forming a component of the parallel resonant circuit. The parallel resonant circuit may be formed from a capacitor connected directly to the inductor, or the capacitor may be coupled to the inductor via intervening components other than a switch. The parallel resonant circuit is configured to generate a pulsed electromagnetic field in the inductor while electrical energy is stored in the parallel resonant circuit. The inductor is configured to be placed relative to a part of a body to provide the pulsed electromagnetic field to the part of the body. The pulsed electromagnetic field therapy device further comprises a power source and a switch, where the switch is external to the parallel resonant circuit. That is, the switch is not located between the capacitor and the inductor in the parallel resonant circuit. Rather, the switch selectively connects the power source parallel to the parallel resonant circuit. The switch is configured to selectively connect the parallel resonant circuit to the power source for a current ramping period. During the current ramping period, a current in the inductor is increased to reach a desired current.

Unlike prior art pulsed electromagnetic field therapy devices, the pulsed electromagnetic field therapy device of the present invention has a parallel resonant circuit which does not require a switch (such as a semiconductor or spark gap switch) to be an integral component of the parallel resonant circuit to selectively power the parallel resonant circuit. By having a switch external to the parallel resonant circuit instead, when current flows around the parallel resonant circuit, it does not pass through a switch on each pass which would unnecessarily dissipate energy stored in the parallel resonant circuit through resistance losses in the switch. Moreover, suitable high voltage switches which can be used as a component of the parallel resonant circuit of a pulsed electromagnetic field therapy device are expensive. Therefore, by having a switch external to the parallel resonant circuit rather than as a component of the parallel resonant circuit, manufacturing costs are significantly reduced and resistance losses from the switch are eliminated. Without these resistance losses from the switch, the decay time of the pulsed electromagnetic field generated by the parallel resonant circuit is greatly increased, thereby increasing the time period over which a physiological effect in generated. Also, the desired current required to obtain a desired time period over which a physiological effect is achieved is much less.

Moreover, by having a switch external to the parallel resonant circuit rather than as a component of the parallel resonant circuit, it is possible to ramp the current over a period of time (the current ramping period). In contrast, prior art pulsed electromagnetic field therapy devices with a switch as a component of the parallel resonant circuit cause charge from the pre-charged capacitor to be dumped nearly instantaneously into the resonant circuit when the switch in the parallel resonant circuit is closed. The high voltages in the prior art, which are necessary to achieve the high currents needed to overcome resistance losses in the high voltage switch, cause a surge of current in the resonant circuit as soon as the switch is closed. This sudden surge in current in the resonant circuit can result in reflections from the high voltage switch (which intrinsically lacks impedance matching with the resonant circuit) resulting in significant voltage and current spikes and electromagnetic interference which can be harmful to nearby electrical devices. In contrast, increasing the current over the current ramping period, which is made possible by the switchless parallel resonant circuit of the present invention, reduces noise and interference caused by the pulsed electromagnetic field therapy device, which helps the pulsed electromagnetic field therapy device meet regulatory requirements, such as regulations regarding electromagnetic interference.

Pulsed electromagnetic fields may be used to provide a physiological effect. For example, a pulsed electromagnetic field may be used for nerve or brain stimulation, or for providing therapeutic benefits (such as treating ailments like joint and muscle pain, and assisting with the healing of broken bones and fractures). The inductor may be placed adjacent to, or around, a part of the body (such as a joint or limb) where the physiological effect of the pulsed electromagnetic field is required. The inductor may be a coil looped inductor. The coil looped inductor may be placed adjacent to, or around, a part of the body (such as a joint or limb) where the physiological effect of the pulsed electromagnetic field is required.

The switch external to the parallel resonant circuit is closed during the current ramping period. The switch external to the parallel resonant circuit is open outside the current ramping period. Therefore, during oscillation of the parallel resonant circuit, the switch is disconnected from the parallel resonant circuit and does not dissipate the energy stored in the parallel resonant circuit through resistance losses nor does the switch lead to reflections.

A charge stored in the capacitor before the switch external to the parallel resonant circuit is closed may be zero.

A current in the inductor may be increased over the current ramping period. The rate of change of the current in the inductor may be a function of the power source voltage. The length of the current ramping period may be based on the power source voltage and the desired current at the end of the current ramping period.

The current ramping period may be one of: greater than 1 µs; greater than 10 µs; between 1 µs and 50 µs; between 10 µs and 50 µs; and between 10 µs and 100 µs, preferably between 1 µs and 100 µs;

The desired current at the end of the current ramping period may be in the range of one of: 10 A and 2000 A; 100 A and 2000 A; 200 A and 2000 A; 200 A and 1600 A; and 500 A and 1600 A; preferably 500 A and 2000 A.

The pulsed electromagnetic field may be an oscillation, such as a sinusoidal oscillation, caused by oscillation of the parallel resonance circuit.

The pulsed electromagnetic field may have a frequency of one of: less than 1 MHz; less than 200 KHz; and less than 100 KHz; preferably less than 250 KHz. Prior art pulsed electromagnetic field therapy devices are intended to operate at around 250 KHz but with a spread spectrum of up to 300 MHz as a result of interference. Operating at these high frequencies, and producing even higher frequencies through interference, means that prior art pulsed electromagnetic field therapy devices are prone to interfering with other electronic devices and radio communications networks. However restrictions on the availability of electronic components, the physical size of electronic components, and the presence of the semiconductor switch in the parallel resonant circuit make it difficult for prior art pulsed electromagnetic field therapy devices to operate at lower frequencies. However, without the limitation of having a high voltage switch in the parallel resonant circuit and instead having the switch external to the parallel resonant circuit, the pulsed electromagnetic field therapy device of the present invention can operate at lower frequencies, which prevents the pulsed electromagnetic field therapy device from interfering with other electronic devices and radio communications networks.

The switch external to the parallel resonant circuit may be open while the parallel resonant circuit is generating at least a portion of the pulsed electromagnetic field. Because the switch in the prior art forms an integral part of the parallel resonant circuit, acting to form at least a part of the electrical connection between the inductor and capacitor of the parallel resonant circuit, the switch necessarily has to be closed for the resonant circuit of the prior art to generate a pulsed electromagnetic field, which leads to resistance losses in the switch. In contrast, in the present invention, the switch is external to the parallel resonant circuit and does not form a necessary link between the inductor and capacitor of the parallel resonant circuit. Therefore, the switch can be open while the parallel resonant circuit generates the pulsed electromagnetic field (oscillates) avoiding resistance losses in the switch.

The parallel resonant circuit may be galvanically isolated from the power source. The inductor and other components of the parallel resonant circuit are floating, and therefore safe to touch even if insulation surrounding the inductor or other components were damaged. The galvanic isolation may comprise a transformer.

The pulsed electromagnetic field therapy device may comprise a further switch external to the parallel resonant circuit and a rectifier to selectively couple the parallel resonant circuit back to a capacitor of the power supply. Closing the further switch may recharge the capacitor of the power supply from the parallel resonant circuit. This substantially reduces oscillation of the parallel resonant circuit and allows at least a portion of the electrical energy remaining in the parallel resonant circuit to be recycled back into the power supply capacitor.

The power supply may be a single high value capacitor, or a capacitor bank comprising a plurality of capacitors.

The further switch may couple the parallel resonant circuit to the power supply when the current in the parallel resonant circuit is below a current threshold. The current threshold may be selected based on a current below which little or no significant physiological effect is observed, or below which insufficient physiological effect is observed to meet the needs of a particular physiological or therapeutic application. The physiological current threshold may be 200 A. Once the current in the parallel resonant circuit has dropped below the current threshold, the further switch and rectifier may couple the parallel resonant circuit back to the power supply, thereby recycling at least some of the electrical energy stored in the parallel resonant circuit back into the power supply, which saves considerable electrical energy that might otherwise be wasted generating a pulsed electromagnetic field which provides little or no physiological benefit.

The switch external to the parallel resonant circuit and/or further switch may receive switching signals over an optical link, for example, a fibre optic cable. Providing switching signals over an optical link reduces high voltage interference which might cause incorrect switching and helps to maintain the galvanic isolation of the parallel resonant circuit. The switch external to the parallel resonant circuit and/or further switch may be controlled by a controller.

The device may be configured to generate a pulsed electromagnetic field discontinuously. The current in the inductor may be ramped and the charge in the parallel resonant circuit may be allowed to decay (or may be quenched, for example, using the further switch). The current may be ramped again immediately or a period of time (such as 100 ms) may be allowed to elapse before the current is ramped again. Having a period when the device is not generating a pulsed electromagnetic field may be desirable to avoid overexposure of a patient to the pulsed electromagnetic field. The duty cycle may be less than 5% (that is, the device may generate a pulsed electromagnetic field for 5% of the time while the device is not generating a pulsed electromagnetic field for 95% of the time). Alternatively, the duty cycle may be less than 1%.

According to a second aspect of the invention, there is provided a method of generating a pulsed electromagnetic field. The pulsed electromagnetic field may be used to provide a physiological effect. For example, a pulsed electromagnetic field may be used for nerve or brain stimulation, or for providing therapeutic benefits (such as treating ailments like joint and muscle pain, and assisting with the healing of broken bones and fractures).

The method comprises generating a pulsed electromagnetic field having a maximum current between 10 A and 2000 A and a maximum voltage between 100 V and 2000 V. Existing techniques for generating a pulsed electromagnetic field for providing a physiological effect involve generating a pulsed electromagnetic field having a much higher maximum voltage (typically 10 kV to 30 kV) in order to achieve sufficient current to overcome resistance losses in a resonant circuit, for example, caused by a high voltage switch in the resonant circuit. Without these resistance losses (for example, because the pulsed electromagnetic field of the present invention is generated in a switchless parallel resonant circuit), it is possible to generate a pulsed electromagnetic field for providing a physiological effect with a lower maximum current and voltage, while also having an improved decay time.

The decay time may be a time period between a maximum and substantially zero current of the pulsed electromagnetic field. For example, the decay time may be at least one of: 100 μs; 200 μs; 300 μs; 400 μs; 500 μs; 600 μs; 700 μs; 800 μs; 900 μs; 1000 μs; 1100 μs; 1200 μs; 1300 μs; 1400 μs; 1500 μs; 1600 μs; 1700 μs; 1800 μs; 1900 μs; and 2000 μs. In contrast, prior art techniques of generating a pulsed electromagnetic field for providing a physiological effect have a much shorter decay time of less than 100 μs, and typically as low as 60 μs, due to resistance losses caused by a semiconductor switch inside the resonant circuit.

The pulsed electromagnetic field may be generated by ramping a current in an inductor with a power supply having a voltage of between 50 V and 400 V.

The inductor may be a component in a switchless parallel resonant circuit.

The current in the inductor may be ramped over a period of greater than 1 μs; greater than 10 μs; between 1 μs and 50 μs; between 10 μs and 50 μs; and between 10 μs and 100 μs; preferably between 1 μs and 100 μs. By generating the pulsed electromagnetic field in a switchless parallel resonant circuit, it is possible to ramp the current in the inductor over a period of time (the current ramping period). In contrast, prior art techniques for generating a pulsed electromagnetic field for providing a physiological effect rely upon a resonant circuit with a switch as a component of the resonant circuit, where closing the switch causes charge from the pre-charged capacitor to be dumped nearly instantaneously into the resonant circuit when the switch in the resonant circuit is closed. The high voltages in the prior art, which are necessary to achieve the high currents needed to overcome resistance losses in such a high voltage switch in the resonant circuit, cause a surge of current in the resonant circuit as soon as the switch is closed. This sudden surge in current in the resonant circuit can result in reflections from the high voltage switch (which intrinsically lacks impedance matching with the resonant circuit) resulting in significant current spikes and electromagnetic interference which can be harmful to nearby electrical devices. In contrast, increasing the current in the inductor over the current ramping period, which is made possible by the switchless parallel resonant circuit of the present invention, reduces noise and interference in the pulsed electromagnetic field, which helps devices which generate this pulsed electromagnetic field meet regulatory requirements, such as regulations regarding electromagnetic interference The pulsed electromagnetic field has a frequency of one of: less than 1 MHz; less than 200 KHz, and less than 100 KHz; preferably less than 250 KHz. Prior art techniques for generating a pulsed electromagnetic field for providing a physiological effect are intended to operate at around 250 KHz but with a spread spectrum of up to 300 MHz as a result of interference. Operating at these high frequencies, and producing even higher frequencies through interference, means that prior art techniques for generating a pulsed electromagnetic field for providing a physiological effect are prone to interfering with other electronic devices and radio communications networks. However restrictions on the availability of electronic components, the physical size of electronic components, and the presence of a switch as a component of the resonant circuit prevents prior art techniques for generating a pulsed electromagnetic field for providing a physiological effect from operating at lower frequencies. However, without the limitation of having a high voltage switch in the parallel resonant circuit, the method for generating a pulsed electromagnetic field therapy for providing a physiological effect according to the present invention can operate at lower frequencies, which helps to prevent devices which generate this pulsed electromagnetic field from interfering with other electronic devices and radio communications networks.

The pulsed electromagnetic field may be generated discontinuously. The current in the inductor may be ramped and the charge in the parallel resonant circuit may be allowed to decay (or may be quenched). The current may be ramped again immediately or a period of time (such as 100 ms) may elapse before the current is ramped again. Having a period when the device is not generating a pulsed electromagnetic field is desirable to avoid overexposure of a patient to the pulsed electromagnetic field. The duty cycle of the pulse electromagnetic field may be less than 5% (that is, the pulsed electromagnetic field may be generated for 5% of the time while the pulsed electromagnetic field is not generated for 95% of the time). Alternatively, the duty cycle may be less than 1%.

BRIEF DESCRIPTION OF THE DRAWINGS

The invention shall now be described, by way of example only, with reference to the accompanying drawings in which.

DETAILED DESCRIPTION

Figure 1:
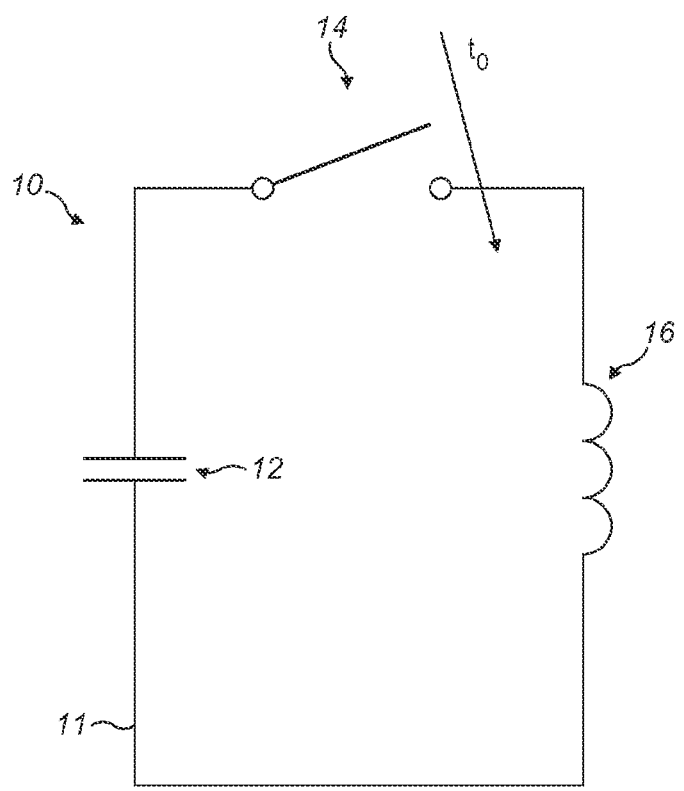
FIG. 1 is a simplified circuit diagram of a prior art pulsed electromagnetic field therapy device.

FIG. 1 is a simplified circuit diagram of a prior art pulsed electromagnetic field therapy device 10. The pulsed electromagnetic field therapy device 10 has a resonant circuit 11 with a capacitor 12 connected to a semiconductor switch 14 and a coil looped inductor 16.

When the semiconductor switch 14 is open, the capacitor 12 is charged from a high voltage circuit (not shown). Closing the semiconductor switch 14 discharges the capacitor 12 into the coil looped inductor 16, initiating oscillation of the resonant circuit 11.

Figure 2A:
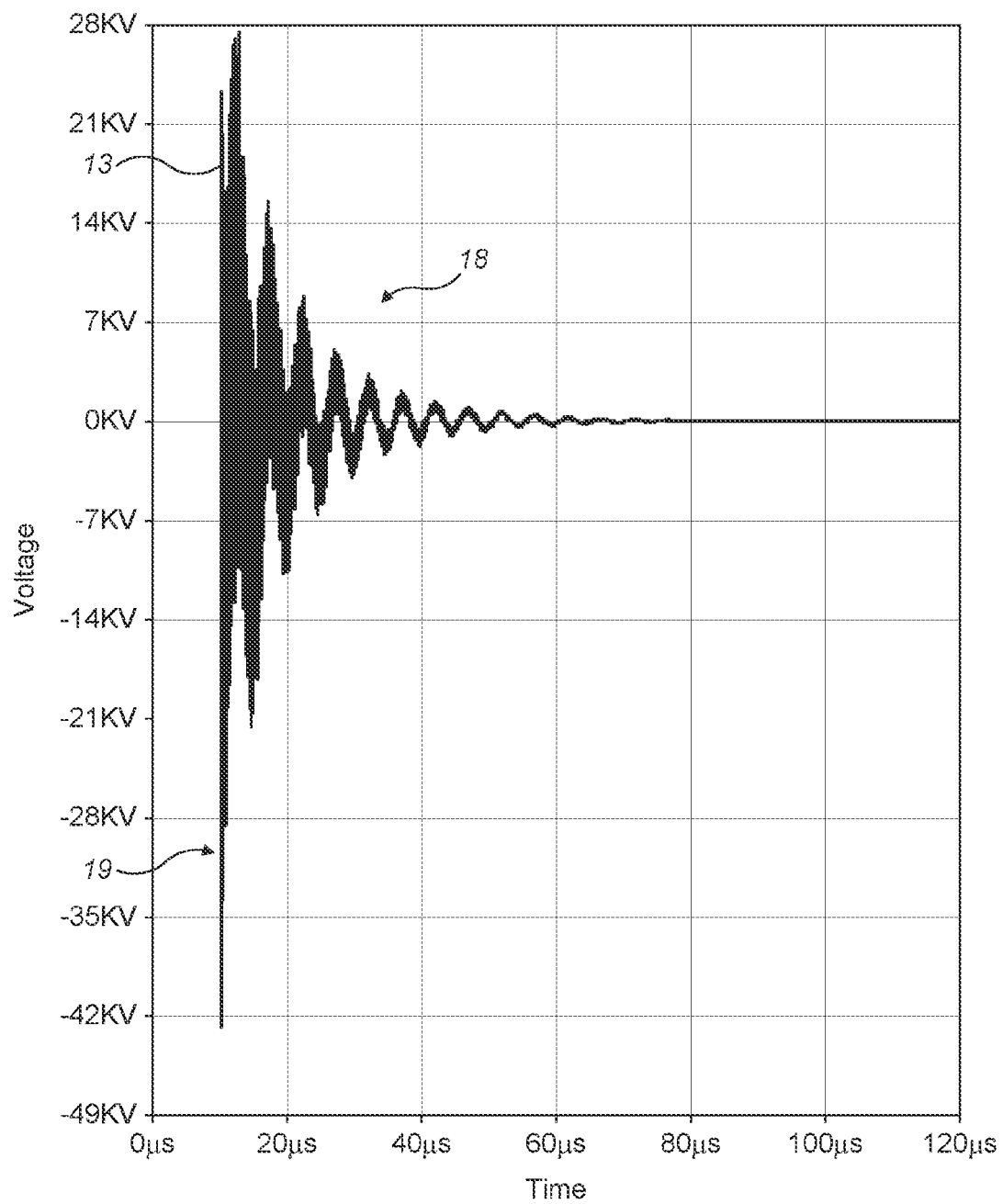
FIG. 2a is an example of an oscilloscope trace showing voltage as a function of time in a resonant circuit of the prior art pulsed electromagnetic field therapy device of FIG. 1.
Figure 2B:
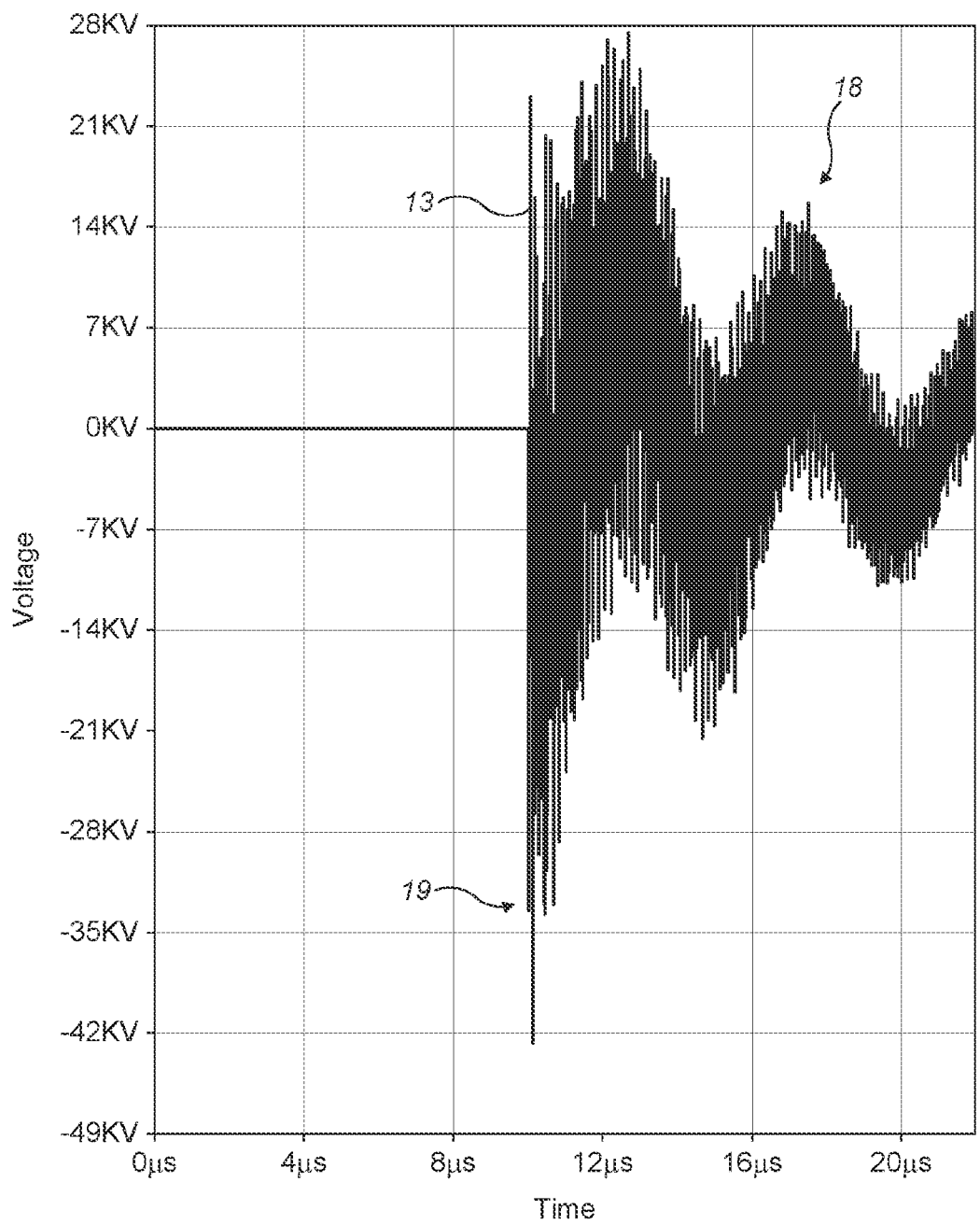
FIG. 2b is a close-up of the oscilloscope trace in FIG. 2a, illustrating interference observed at the start of the electromagnetic oscillations in the prior art pulsed electromagnetic field therapy device of FIG. 1.

FIGS. 2a and 2b show different views of the same oscilloscope trace of the voltage in the resonant circuit 11 as a function of time. The resonant circuit 11 generates a damped oscillation 18 in the coil looped inductor 16. FIG. 2a shows the entire sequence of oscillations until the oscillations completely decay, while FIG. 2b shows a close-up view of the start of the oscillations.

The coil looped inductor 16 is placed adjacent to, or around, a part of the body (such as a limb or joint) where the physiological effect of the pulsed electromagnetic field is desired.

With the semiconductor switch 14 closed, the resonant circuit 11 oscillates until losses in the resonant circuit 11 dissipate all of the energy stored in the resonant circuit 11. Resistance losses in the resonant circuit 11 are high. The semiconductor switch 14 being an integral part of the electrical connection between the coil looped inductor 16 and the capacitor 12 in the resonant circuit 11 incurs resistance losses which quickly cause the energy stored in the resonant circuit 11 to decay. Rapid decay limits the time period over which a pulsed electromagnetic field provides a physiological effect. In an attempt to maximise the decay time, the capacitor 12 is charged to a high voltage (typically 10 kV-25 kV) to achieve a high discharge current (of the order of 2 kA-3 kA).

The need to operate at such a high voltage and current cause a whole host of issues with the design and operation of the pulsed electromagnetic field therapy device 10. An expensive high voltage capacitor 12 and semiconductor switch 14 is required, which makes it expensive to manufacture the pulsed electromagnetic field therapy device 10. Additionally, the high voltages represent a safety risk to the operator and patient, particularly as the design of many existing pulsed electromagnetic field therapy devices, like the pulsed electromagnetic field therapy device 10, do not take steps to prevent lethal single point failures, for example, in a case where the insulation of the coil looped inductor 16 becomes damaged.

The high voltage to which the capacitor 12 is initially charged causes a high initial current discharge from the capacitor 12 which leads to voltage reflections from components within the resonant circuit 11, particularly the semiconductor switch 14. Given the complicated electrical characteristics of semiconductor switch 14 which are needed to handle the high voltages and currents present in the resonant circuit 11, it is virtually impossible to impedance match the semiconductor switch 14 with the rest of the resonant circuit 11. As a result of the impedance mismatch, the semiconductor switch 14 causes voltage reflections which lead to high power broad spectrum radio-frequency interference 19 being observed for the first few microseconds of the electromagnetic oscillations (as shown in FIG. 2b). Such radio-frequency interference causes the pulsed electromagnetic field therapy device 10 to interfere with other electronic devices or wireless communications networks in the vicinity, and may mean that the pulsed electromagnetic field therapy device 10 does not meet regulatory requirements, such as regulations regarding electromagnetic interference.

Figure 3:
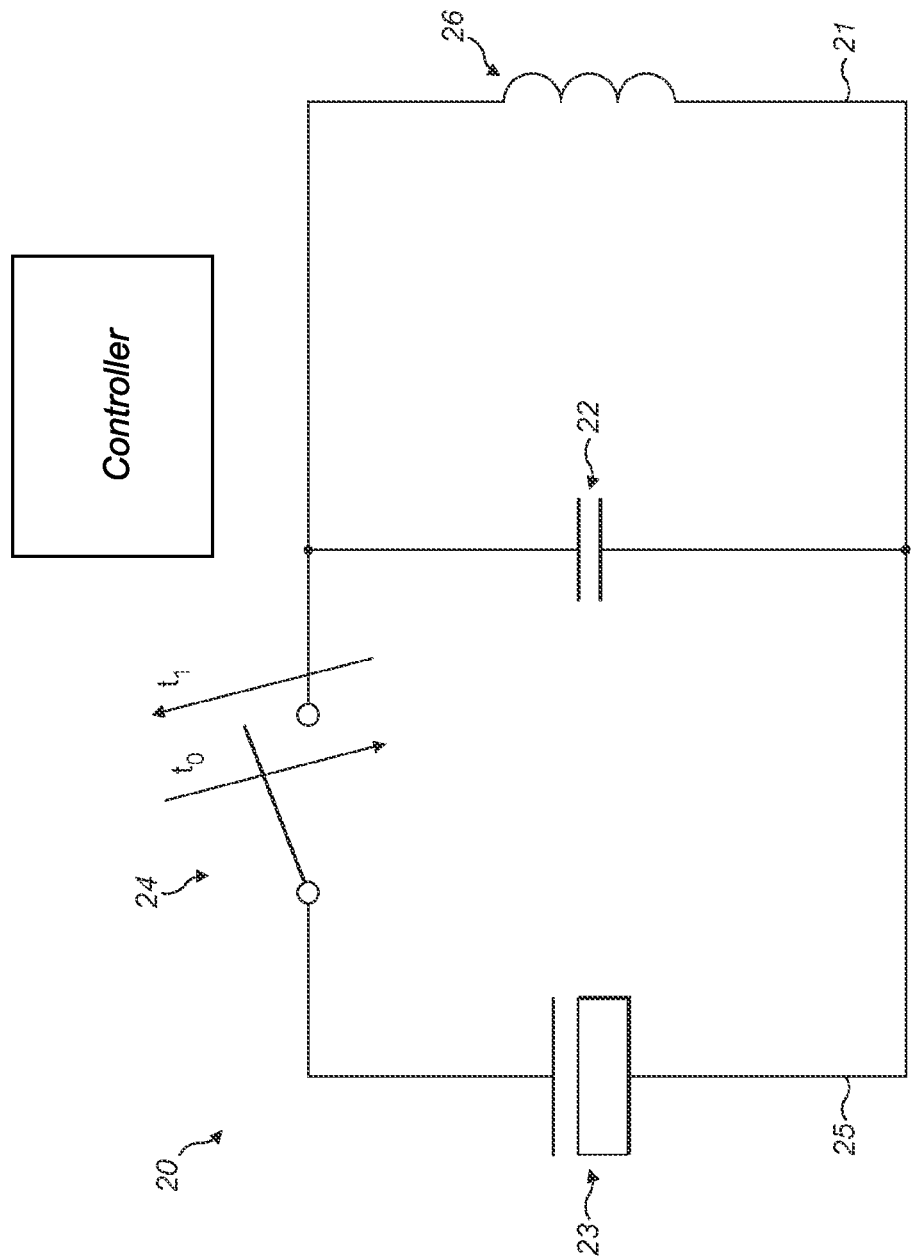
FIG. 3 illustrates a pulsed electromagnetic therapy device according to an embodiment of the present invention.

FIG. 3 illustrates a pulsed electromagnetic field therapy device 20 according to an embodiment of the present invention. The pulsed electromagnetic field therapy device 20 has been designed to overcome the above-mentioned shortcomings with existing pulsed electromagnetic field therapy devices, such as pulsed electromagnetic field therapy device 10 described in relation to FIGS. 1 and 2.

The pulsed electromagnetic field therapy device 20 has a parallel resonant circuit 21 with a capacitor 22 in parallel with a coil looped inductor 26. A current ramping circuit 25 is external to the parallel resonant circuit 21 and connected in parallel to the parallel resonant circuit 21. The current ramping circuit 25 includes a high current capability capacitor 23 which provides a voltage of around 50 V-350 V (typically 150 V) and a current of around 100 A-2000 A. A semiconductor switch 24 selectively connects the high current capability capacitor 23 to the parallel resonant circuit 21 to ramp-up the current in the coil looped inductor 26.

Figure 4:
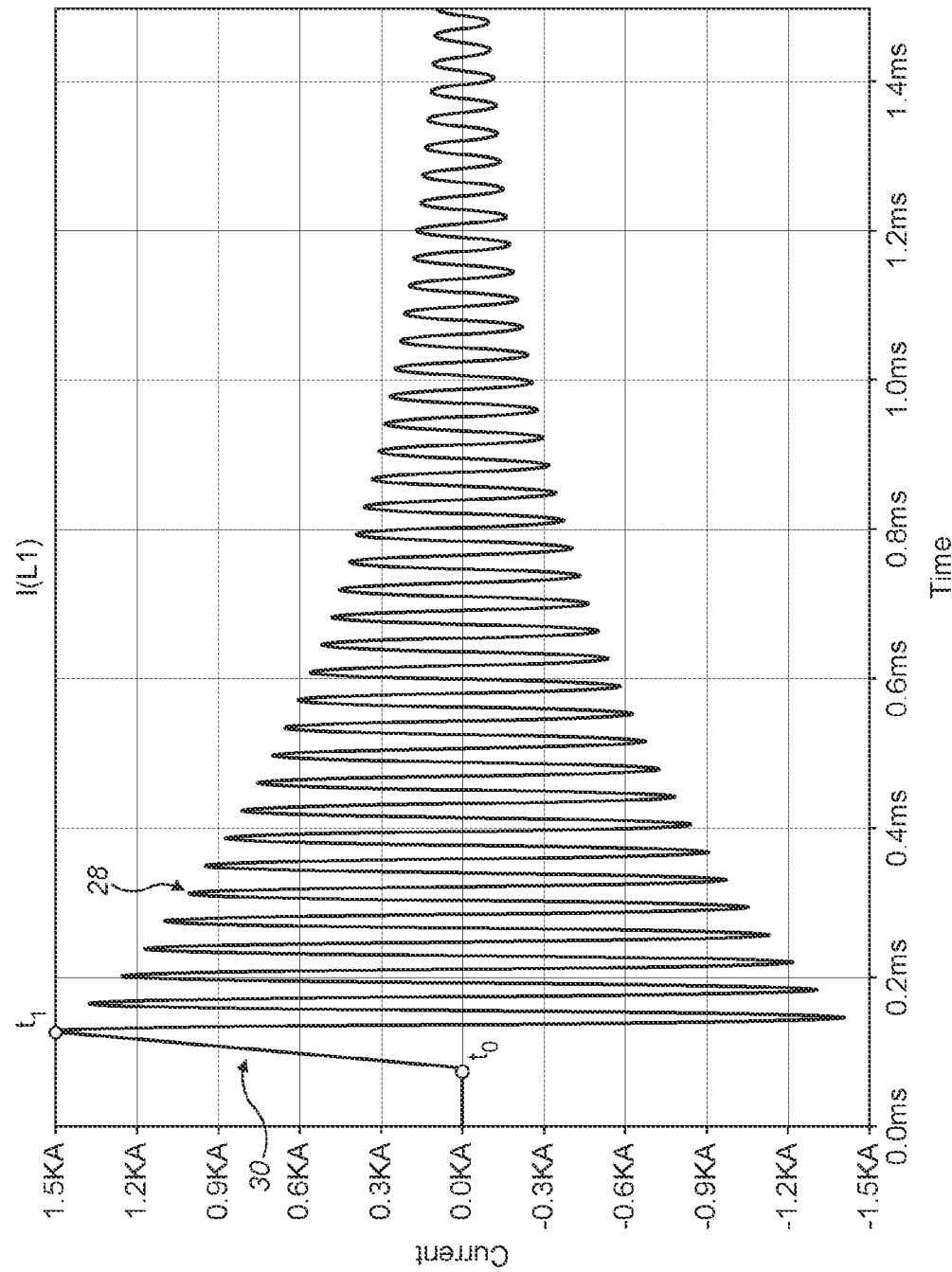
FIG. 4 is an example of an oscilloscope trace showing the current in the resonant circuit of FIG. 3 as a function of time.

The oscilloscope trace in FIG. 4 shows the current in the parallel resonant circuit 21 as a function of time. The semiconductor switch 24 is closed at $t_0$ for a current ramping period (indicated by reference numeral 30 in FIG. 4) of about 50 μs to ramp-up the current in the coil looped inductor 26. At the end of the current ramping period at $t_1$, the semiconductor switch 24 is opened, disconnecting the current ramping circuit 25 from the parallel resonant circuit 21 and preventing further increase in the current in the coil looped inductor 26. At the end of the current ramping period, the current in the coil looped inductor 26 has reached a desired current of 1500 A, which is sufficient to provide a physiological effect.

At the end of the current ramping period at $t_1$, and with the semiconductor switch 24 open, the current in the coil looped inductor 26 initiates oscillation of the parallel resonant circuit 21. As illustrated by the oscilloscope trace in FIG. 4, the parallel resonant circuit 21 generates a sequence of damped sinusoidal oscillations 28 in the coil looped inductor 26. The coil looped inductor 26 is placed adjacent to, or around, a part of the body (such as a limb or joint) where the physiological effect of the pulsed electromagnetic field is desired.

The parallel resonant circuit 21 oscillates until losses in the parallel resonant circuit 21 dissipate all of the energy stored in the parallel resonant circuit 21.

An important difference over the pulsed electromagnetic field therapy device 10 is that the semiconductor switch 24 does not need to be a component of the parallel resonant circuit 21 in order to control current within the coil looped inductor 26. Instead, current ramping of the parallel resonant circuit 21 is controlled by current ramping circuit 25 which is external to and connected in parallel to the parallel resonant circuit 21. Not having a semiconductor switch 14 as a component of the parallel resonant circuit 21 provides a number of benefits.

Resistance losses in the parallel resonant circuit 21 are low because the semiconductor switch 24 is external to the parallel resonant circuit 21, so resistance losses from the semiconductor switch 24 are not incurred during oscillation of the parallel resonant circuit 21. As a result, the decay time of the damped oscillations is much longer which increases the time period over which the pulsed electromagnetic field provides a physiological effect for a given initial current in the coil looped inductor 26. For example, a physiological effect may be present when the current in the parallel resonant circuit 21 is greater than around 200 A, and the pulsed electromagnetic field therapy device 20 enjoys a period of around 1100 µs in which the current in the parallel resonant circuit 21 is providing a physiological effect, as compared with only 60 µs with the pulsed electromagnetic field therapy device 10. As a result, the pulsed electromagnetic field therapy device 20 provides a more sustained physiological effect. Moreover, the coil looped inductor 26 need only be ramped to a lower initial current (only 200 A-1500 A in the pulsed electromagnetic field therapy device 20 as compared with 2000 A-3000 A in the pulsed electromagnetic field therapy device 10), leading to lower voltages in the pulsed electromagnetic field therapy device 20 which do not require capacitor 22 or semiconductor switch 24 to be expensive high voltage components, reducing manufacturing costs. Additionally, operating at lower voltages allows capacitor 22 to have a larger capacitance value than a higher voltage capacitor of equivalent physical size, and the selection of a larger capacitance value for capacitor 22 leads to parallel resonant circuit 21 having a lower resonant frequency which allows the pulsed electromagnetic field therapy device 20 to meet regulatory requirements regarding electromagnetic interference.

In the pulsed electromagnetic field therapy device 10, the charge from the capacitor 12 is dumped into the resonant circuit 11 nearly instantaneously (at point 13 on FIGS. 2a and 2b) when the semiconductor switch 14 in the resonant circuit 11 is closed. As discussed above, this rapid charge discharged into the resonant circuit 11 leads to current reflections which result in significant interference 19. By not having semiconductor switch 24 as a component of the parallel resonant circuit 21, the current in the parallel resonant circuit 21 is increased more gradually over the course of the current ramping period 30. This, combined with the fact that the semiconductor switch 24 is external to and disconnected from the parallel resonant circuit 24 after the current ramping period 30 so that the impedance mismatched semiconductor switch 24 does not lead to reflections, results in a current profile (FIG. 4) in the parallel resonant circuit 21 which is sinusoidal with low distortion, and which does not show the large amount of interference 19 (FIGS. 2a and 2b) seen in the pulsed electromagnetic field therapy device 10.

Figure 5:
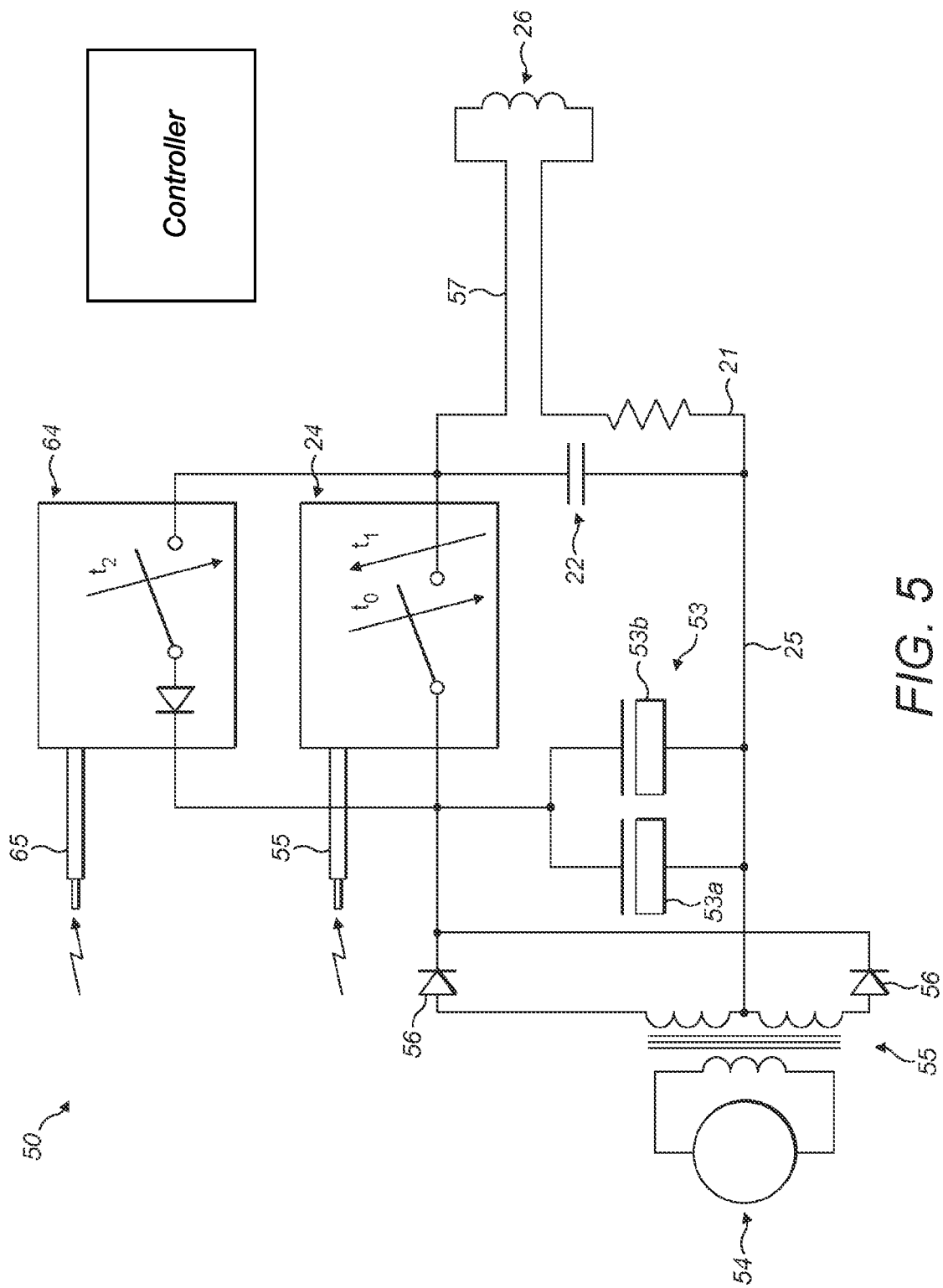
FIG. 5 is an example of a pulsed electromagnetic field therapy device according to an alternative embodiment of the present invention.

FIG. 5 illustrates a pulsed electromagnetic field therapy device 50 according to an alternative embodiment of the present invention. The pulsed electromagnetic field therapy device 50 is generally the same as the pulsed electromagnetic field therapy device 20, with some improvements to electrical safety, charging and control.

The pulsed electromagnetic field may show no significant physiological effect once the current in the parallel resonant circuit 21 has dropped below a certain current (for example, once the current in the parallel resonant circuit 21 has dropped below 200 A). Therefore, a current threshold may be selected based on a current below which little or no significant physiological effect is observed, or below which insufficient physiological effect is observed to meet the needs of a particular physiological or therapeutic application.

Once the current in the parallel resonant circuit 21 has dropped below the current threshold (at time $t_2$), a further switch 64 is closed which connects the parallel resonant circuit 21 to the capacitor bank 53. This substantially reduces oscillation of the parallel resonant circuit 21 and allows at least part of the energy remaining in the parallel resonant circuit 21 to be recycled to at least partially recharge the capacitor bank 53. This saves considerable energy that might otherwise be wasted generating a pulsed electromagnetic field which provides no physiological effect.

Instead of a single high current capability capacitor 23, the pulsed electromagnetic field therapy device 50 has a capacitor bank 53 which is made up of capacitors 53a and 53b connected in parallel which together offer a high current capability source. The use of capacitor bank 53 may provide redundancy in case a capacitor 53a or 53b fails, and may be cheaper than using a single high current capability capacitor 23. The capacitor bank 53 could provide a high current capability source using more than two capacitors. In fact, it may be beneficial for the capacitor bank 53 to combine a large number of cheap, lower value capacitors which are smaller and therefore easier to pack into spare space in a housing.

The capacitor bank 53 is charged from power source 54 which is in turn fed from a mains electricity supply. To improve electrical safety, and reduce the risk of a patient or operator receiving an electrical shock from the high voltages and currents present in the current ramping circuit 25 and the parallel resonant circuit 21, the current ramping circuit 25 and the parallel resonant circuit 21 are galvanically isolated from the power source 54 by transformer 55 and diodes 56. Therefore, the inductor 26 and other components of the parallel resonant circuit 21 are floating, and therefore safe to touch even if insulation surrounding the inductor 26, cable 57 or other components is damaged.

To complete the isolation, the semiconductor switch 24 receives switching signals over a fibre optic cable 55 and the optional further switch 64 receives switching signals over a fibre optic cable 65. This helps to reduce induced interference which might occur on an electrical link.

Although the invention has been described in relation to particular embodiments. The skilled person will appreciate that various modifications could be made based on other aspects of the disclosure without departing from the scope of the claims.

The invention claimed is:

1. A pulsed electromagnetic field therapy device comprising:
 a parallel resonant circuit comprising a capacitor connected in parallel with an inductor without a switch between the capacitor and the inductor in the parallel resonant circuit;
 a power source having a voltage of between 50 V and 400 V;
 a switch, external to the parallel resonant circuit, and connected in between the power source and the parallel resonant circuit; and
  a controller which is configured to: close the switch to connect the parallel resonant circuit to the power source for a current ramping period during which a current in the inductor is increased to reach a predetermined current between 10 A and 2000 A, and open the switch at an end of the current ramping period to disconnect the parallel resonant circuit from the power source, wherein the parallel resonant circuit generates a pulsed electromagnetic field comprising a sequence of damped sinusoidal electromagnetic oscillations in the inductor while electrical energy is stored in the parallel resonant circuit and whilst the switch is open,
  wherein the inductor is configured to be placed relative to a part of a body to provide the pulsed electromagnetic field to the part of the body.

2. The device of claim 1, wherein a charge stored in the capacitor before the switch external to the parallel resonant circuit is closed is zero.

3. The device of claim 1, wherein the current ramping period is one of: greater than 1 μs; greater than 10 μs; between 1 μs and 50 μs; between 10 μs and 50 μs; between 1 μs and 100 μs; and between 10 μs and 100 μs.

4. The device of claim 1, wherein the predetermined current is in the range of one of: 100 A and 2000 A; 200 A and 2000 A; 200 A and 1600 A; 500 A and 1600 A; and 500 A and 2000 A.

5. The device of claim 1, wherein the pulsed electromagnetic field has a frequency comprising: less than 1 MHz; less than 250 KHz; less than 200 KHz or less than 100 KHz.

6. The device of claim 1, wherein the inductor is a coil loop inductor.

7. The device of claim 1, wherein the parallel resonant circuit is galvanically isolated from the power source.

8. The device of claim 1, wherein the switch external to the parallel resonant circuit receives switching signals over an optical link.

9. The device of claim 1 further comprising a second switch coupled between the parallel resonant circuit and a capacitor of the power supply, wherein the controller is configured to close the second switch to recharge the power supply capacitor from the parallel resonant circuit.

10. The device of claim 9, wherein the controller is configured to close the second switch to couple the parallel resonant circuit to the power supply when the current in the parallel resonant circuit is below a current threshold.

11. The device of claim 1, wherein the duty cycle is 5% or less, or 1% or less.

12. A method of generating a pulsed electromagnetic field for providing a physiological effect, the method comprising:
 generating a pulsed electromagnetic field by:
  ramping a current in an inductor of a switchless parallel resonant circuit to reach a desired current between 10 A and 2000 A, by closing a switch connected in between the parallel resonant circuit and a power supply having a voltage of between 50 V and 400 V over a current ramping period to connect the parallel resonant circuit with the power supply over the current ramping period; and
 after the current ramping period, generating a sequence of damped sinusoidal electromagnetic oscillations in the inductor by opening to switch to disconnect the parallel resonant circuit from the power supply.

13. The method of claim 12, wherein the current in the inductor is ramped over a period of: greater than 1 μs; greater than 10 μs; between 1 μs and 50 μs; between 10 μs and 50 μs; between 1 μs and 100 μs; or between 10 μs and 100 μs.

14. The method of claim 12, wherein the pulsed electromagnetic field has a decay time of at least: 100 μs; 200 μs; 300 μs; 400 μs; 500 μs; 600 μs; 700 μs; 800 μs; 900 μs; 1000 μs; 1100 μs; 1200 μs; 1300 μs; 1400 μs; 1500 μs; 1600 μs; 1700 μs; 1800 μs; 1900 μs; or 2000 μs.

15. The method of claim 12, wherein the pulsed electromagnetic field has a frequency of: less than 1 MHz; less than 250 KHz, less than 200 KHz, or less than 100 KHz.

16. The method of claim 12 wherein the duty cycle of the pulsed electromagnetic field is 5% or less, or 1% or less.

17. The method of claim 12, wherein the current in the inductor is ramped over a period of one of: greater than 1 μs; greater than 10 μs; between 1 μs and 50 μs; between 10 μs and 50 μs; between 1 μs and 100 μs; and between 10 μs and 100μ.

* * * * *